US008071641B2

(12) United States Patent
Weiss et al.

(10) Patent No.: US 8,071,641 B2
(45) Date of Patent: Dec. 6, 2011

(54) TREATING OR PREVENTING DIABETES WITH CANNABIDIOL

(75) Inventors: Lola Weiss, Jerusalem (IL); Michael Zeira, Beit-Shemesh (IL); Raphael Mechoulam, Jerusalem (IL); Shimon Slavin, Jerusalem (IL); Ruth Gallily, Jerusalem (IL)

(73) Assignees: Yissum Research Development Company of the Hebrew University of Jerusalem, Jerusalem (IL); Hadsit Hadasit Medical Research Services and Development Ltd., Jerusalem (IL)

( * ) Notice: Subject to any disclaimer, the term of this patent is extended or adjusted under 35 U.S.C. 154(b) by 1370 days.

(21) Appl. No.: 10/589,623

(22) PCT Filed: Feb. 16, 2005

(86) PCT No.: PCT/IL2005/000196
§ 371 (c)(1),
(2), (4) Date: Aug. 16, 2006

(87) PCT Pub. No.: WO2005/077348
PCT Pub. Date: Aug. 25, 2005

(65) Prior Publication Data
US 2007/0099987 A1    May 3, 2007

(30) Foreign Application Priority Data

Feb. 16, 2004 (IL) .......................................... 160420

(51) Int. Cl.
*A61K 31/05* (2006.01)
*A61K 31/192* (2006.01)
*A61K 31/353* (2006.01)

(52) U.S. Cl. .......................... 514/454; 514/568; 514/734
(58) Field of Classification Search .................. 514/454, 514/568, 734
See application file for complete search history.

(56) References Cited

U.S. PATENT DOCUMENTS

| | | | |
|---|---|---|---|
| 4,371,720 | A | 2/1983 | Johnson et al. |
| 5,013,387 | A | 5/1991 | Goodwin et al. |
| 5,081,122 | A | 1/1992 | Ward |
| 5,292,736 | A | 3/1994 | Kumar et al. |
| 5,461,034 | A | 10/1995 | Rodan et al. |
| 5,618,955 | A | 4/1997 | Mechoulam et al. |
| 6,166,066 | A | 12/2000 | Makriyannis et al. |
| 6,403,123 | B1 | 6/2002 | Scott et al. |
| 6,410,588 | B1 | 6/2002 | Feldmann et al. |
| 6,531,636 | B1 | 3/2003 | Mechoulam et al. |
| 7,071,231 | B2 * | 7/2006 | Spevak et al. ................. 514/595 |

FOREIGN PATENT DOCUMENTS

| | | |
|---|---|---|
| EP | 0444451 | 4/1991 |
| EP | 0570920 | 11/1993 |
| FR | 2735774 | 9/1997 |
| WO | WO 94/12466 | 6/1994 |
| WO | WO 94/12466 | 9/1994 |
| WO | WO 97/29079 | 8/1997 |
| WO | WO 98/41519 | 9/1998 |
| WO | WO 99/02499 | 1/1999 |
| WO | WO 99/53917 | 10/1999 |
| WO | WO 00/19773 | 6/2000 |
| WO | WO 02/13814 A1 * | 2/2002 |
| WO | WO 03/063847 | 7/2003 |

OTHER PUBLICATIONS

Gorter Cancer cachexia and cannabinoids. Forschende Komplementarmedizin, 1999 vol. 6, No. Suppl. 3, pp. 21-22. ISSN: 1021-7096.*
Communication Pursuant to Article 94(3) EPC Dated Dec. 18, 2009 From the European Patent Office Re.: Application No. 05703237.7.
International Search Report and the Written Opinion Dated Jun. 21, 2005 From the International Searching Authority Re.: Application No. PCT/IL2005/000196.
Office Action Dated Feb. 1, 2010 From the Israel Patent Office Re.: Application No. 160420 and Its Translation Into English.
Official Action Dated Feb. 16, 2010 From the US Patent and Trademark Office Re.: U.S. Appl. No. 10/589,623.
Adis "Cannabis-Based Medicines—GW Pharmaceuticals. High CBD, High THC, Medicinal Cannabis—GW Pharmaceuticals, THC-:CBD", Drugs R & D, 4(5): 306-309, 2003.
Adams et al. "Isolation of Cannabinol, Cannabidiol and Quebrachitol From Red Oil of Minnesota Wild Hemp", Journal of the American Chemical Society, 62: 2194-2196, 1940.
Burstein et al. "Synthetic Nonpsychotropic Cannabinoids With Potent Antiinflammatory, Analgesic, and Leukocyte Antiadhesion Activities", Journal of Medicinal Chemistry, 35: 3135-3141, 1992.
Coffey et al. "Tetrahydrocannabinol Inhibition of Macrophage Nitric Oxide Production", Biochemical Pharmacology, 52: 743-751, 1996.
Devane et al. "Isolation and Structure of a Brain Constituent That Binds to the Cannabinoid Receptor", Science, 258: 1946-1949, 1992.
Edery et al. "Structural Requirements for Cannabinoid Activity", Annals of the NY Academy of Sciences, 191: 40-53, 1971.
Felder et al. "Anandamide, An Endogenous Cannabimimetic Eicosanoid, Binds to the Cloned Human Cannabinoid Receptor and Stimulates Receptor-Mediated Signal Transduction", Proc. Natl. Acad. Sci. USA, 90: 7656-7660, 1993.
Gaoni et al. "The Isolation and Structure of $\Delta^1$—Tetrahydrocannabinol and Other Neutral Cannbinoids From Hashish", Journal of the American Chemical Society, 93: 217-224, 1971.
Hanuš et al. "Two New Unsaturated Fatty Acid Ethanolamides in Brain That Bind to the Cannabinoid Receptor", Journal of Medicinal Chemistry, 36: 3032-3034, 1993.
Hanuš et al. "2-Arachidonyl Glyceryl Ether, An Endogenous Agonsit of the Cannabinoid CBI Receptor", Proc. Natl. Acad. Sci. USA, 98(7): 3662-3665, 2001.
Houry et al. "Benzoxocin and Bensoxonin Derivatives. Novel Groups of Terpenophenols With Central Nervous System Activity. A Correction", Journal of Medicinal Chemistry, 18(9): 951-952, 1975.
Zuardi et al. "Antipsychotic Effect of Cannabidiol", Journal of Clinical Psychiatry, 56(10): 485-486, 1995.

(Continued)

*Primary Examiner* — Jennifer M Kim

(57) ABSTRACT

Use of a cannabidiol for the manufacture of a medicament identified for the treatment or prevention of diabetes and/or insulitis.

5 Claims, No Drawings

OTHER PUBLICATIONS

Formukong et al. "Analgesic and Antiflammatory Activity of Constituents of Cannabis Sativa L.", Inflammation, 12(4): 361-371, 1988.

Venstrom et al. "Survival After Pancreas Transplantation in Patients With Diabetes and Preserved Kidney Function", JAMA, 290(21): 2817-2823, 2003. Correction: 291(13); 1566, 2004.

Kendall et al. "Pancreas and Islet Transplantation", The Endocrinologist, 5: 28-35, 1995.

Mechoulam "Marijuana: Chemistry, Pharmacology, Metabolism and Clinical Effects", Academic Press, 65: Book Info & Table of Contents, 1973.

Houry et al. "Benzoxocin and Benzoxonin Derivatives. Novel Groups of Terpenophenols With Central Nervous System Activity", Journal of Medicinal Chemistry, 17(3): 287-293, 1974.

Mechoulam et al. "Hashish—I. The Structure of Cannabidiol", Tetrahedron, 19: 2073-2078, 1963.

Mechoulam et al. "Identification of an Endogenous 2-Monoglyceride, Present in Canine Gut, That Binds to Cannabinoid Receptors", Biochemical Pharmacology, 50(1): 83-90, 1995.

Mechoulam et al. "Recent Advances in the Chemistry and Biochemistry of Cannabis", Chemical Reviews, 76(1): 75-112, 1976.

Mechoulam et al. "Synthesis and Biological Activity of Five Tetrahydrocannabinol Metabolites", Journal of the American Chemical Society, 94(22): 7930-7931, 1972.

Mechoulam et al. "Stereochemical Requirements for Cannabinoid Activity", Journal of Medicinal Chemistry, 23(10): 1068-1072, 1980.

Mechoulam et al. "Chemical Basis of Hashish Activity", Science, 169(3945): 611-612, 1970.

Mechoulam et al. "Synthesis of the Indivivdual, Pharmacologically Distinct, Enantiomers of A Tetrahydrocannabinol Derivative", Tetrahedron: Asymmetry, 1(5): 315-318, 1990.

Murphy et al. "Cannabinoid Geometry and Biological Activity", Marijuana/Cannbinoids: Neurobiology and Neurophysiology, p. 1-33, 1992.

Leite et al. "Anticonvulsant Effects of the (−) and (+)Isomers of Cannabidiol and Their Dimethylheptyl Homologs", Pharmacology, 24: 141-146, 1982.

Zuardi et al. "Effects of Cannabidiol in Animal Models Predictive of Antipsychotic Activity", Psychopharmacology, 104(2): 260-264, 1991.

Rhee et al. "Cannabinol Derivatives: Binding to Cannabinoid Receptors and Inhibiton of Adenylylcyclase", Journal of Medicinal Chemistry, 40: 3228-3233, 1997.

Robertson "Seminars in Medicine of the Beth Israel Hospital, Boston: Pancreatic and Islet Transplantation for Diabetes—Cures of Curiosities?", The New England Journal of Medicine, 327(26): 1861-1868.

Petrzilka et al. "Synthese und Chiralität des (−)-Cannabidiols", Helvetica Chimica Acta, 50, Fasciculus 2(73-74/Chap.74): 719-723, 1967.

Sheskin et al. "Structural Requirements for Binding of Anandamide-Type Compounds to the Brain Cannabinoid Receptor", Journal of Mrdicinal Chemistry, 40: 659-667, 1997.

Srebnik et al. "Base-Catalysed Double-Bond Isomerizations of Cannabinoids: Structural and Stereochemical Aspects", Journal of the Chemical Society, Perkin Transactions I, p. 2881-2886, 1984.

Mechoulam et al. "A Total Synthesis of D1-$\Delta^1$—Tetrahydrocannabinol, the Active Constituent of Hashish", Journal of the American Chemical Society, 87(14): 3273-3275, 1965.

Watzl et al. "Influence of Marijuana Components (THC and CBD) on Human Mononuclear Cell Cytokine Secretion in Vitro", Drugs of Abuse, Immunity, and Immunodeficiency, p. 63-70, 1991.

??? "Cannabis-Based Medicines—GW Pharmaceuticals: High CBD, High THC, Medicinal Cannabis—GW Pharmaceuticals, THC: CBD", Drugs R&D, 4(5): 306-309, 2003. p. 307, 4th Full §.

Weiss et al. "Cytokine Production in Linomide-Treated Nod Mice and the Potential Role of A Th1/Th2 Shift on Autoimmune and Anti-Inflammatory Processes", Cytokine, 19(2): 85-93, 2002. Fig.1, 4, p. 87-91, § entitled "Discussion".

Srivastava et al. "$\Delta 9$ Tetrahydrocannabinol and Cannabidiol Alter Cytokine Production by Human Immune Cells", Immunopharmacology, 40(3): 179-185, 1998. p. 183-184, § entitled "Discussion".

Response Dated Sep. 27, 2010 to Communication Pursuant to Article 94(3) EPC of Dec. 18, 2009 From the European Patent Office Re.: Application No. 05703237.7.

Communication Pursuant to Article 94(3) EPC Dated Nov. 29, 2010 From the European Patent Office Re.: Application No. 05703237.7.

Response Dated May 22, 2011 to Communication Pursuant to Article 94(3) EPC of Nov. 29, 2010 From the European Patent Office Re.: Application No. 05703237.7.

Office Action Dated Feb. 11, 2009 From the Israeli Patent Office Re.: Application No. 160420 and Its Translation Into English.

* cited by examiner

TREATING OR PREVENTING DIABETES WITH CANNABIDIOL

RELATED APPLICATIONS

This application is a National Phase Application of PCT Patent Application No. PCT/IL2005/000196 having International Filing Date of Feb. 16, 2005, which claims the benefit of Israel Application No. 160420 filed on Feb. 16, 2004. The contents of the above Applications are all incorporated herein by reference.

FIELD AND BACKGROUND OF THE INVENTION

The present invention relates to the use of a cannabidiol for treating or preventing diabetes and related disorders.

Diabetes is a disease characterized by failure of insulin feedback and secretion in the beta cells of the pancreatic islets of Langerhans and is one of the most common endocrine diseases across all age groups and populations. The most obvious metabolic effect in diabetes is chronic, erratic elevation of the blood glucose level which is associated with progressive damage to blood vessels. This may lead to heart attack, stroke, blindness, peripheral nerve dysfunction, and kidney failure. Presently there are 18.2 million people in the United States alone who have diabetes. In addition to the clinical morbidity and mortality, the economic cost of diabetes is huge, exceeding $90 billion per year in the United States alone, and the prevalence of diabetes is expected to increase more than two-fold by the year 2010.

There are two major forms of diabetes mellitus: insulin-dependent (Type I) diabetes mellitus which accounts for 5 to 10% of all cases, and non-insulin-dependent (Type II) diabetes mellitus which comprises roughly 90 to 95% of cases.

Type I diabetes mellitus is an autoimmune disease characterized by progressive destruction of pancreatic beta-cells and most often occurring in children and young adults. The disease is associated with high rate of severe irreversible complications which occur despite the availability of insulin replacement, usually through injections administered 1-4 times daily.

Most therapeutic strategies for treatment or prevention of type I diabetes mellitus are directed to suppression of the autoimmune response in order to prevent beta-cell destruction. Accordingly, various immunosuppressive agents have been considered for preventing destruction of pancreatic beta-cells have been attempted, such as glucocorticoids, cyclophosphamide, cyclosporin A, rapamycin, FK506 and prodigiosin. However, the use of such immunosuppressive agents may cause severe side effects such as drug-related toxicity to liver or kidney and to increase incidence of infectious complications, particularly in patients with diabetes mellitus that are already susceptible to infections as part of their disease.

Type II diabetes results from a loss of insulin production combined with body's inability to properly use insulin, and is oftentimes associated with aging. In Type II diabetes, patients typically begin therapy by following a regimen of an optimal diet, weight reduction and exercise. Drug therapy is initiated when these measures no longer provide adequate metabolic control. Initial drug therapy includes sulfonylureas (for example, tolbutamide, chlorpropamide and glibenclamide), biguanides (for example, metformin and buformin) and α.-glucosidase inhibitors (for example, acarbose and voglibose). However, over 50% of all diabetics treated by presently available drugs demonstrate poor glycemic control within six years, and require insulin replacement therapy as the last resort.

Although many of the symptoms of diabetes mellitus may be controlled by insulin therapy, the long-term complications of both type I and type II diabetes mellitus are severe and may reduce life expectancy by as much as one third. Over time, elevated blood glucose levels damage blood vessels, the heart, eyes, kidneys, nerves, autonomic nervous system, skin, connective tissue, and white blood cell function.

Moreover, insulin therapy may result in insulin allergy, insulin resistance, atrophy of the subcutaneous fat at the site of insulin injection (i.e., lipoatrophy), enlargement of subcutaneous fat deposit (i.e., lipohypertrophy) due to lipogenic action of high local concentration of insulin, and insulin edema.

There is thus a widely recognized need for, and it would be highly advantageous to have new, safe and effective therapies for diabetes mellitus. Accordingly, the present invention provides a novel method and an article of manufacture for treating or preventing diabetes mellitus and related disorders.

SUMMARY OF THE INVENTION

According to one aspect of the present invention there is provided use of a cannabidiol for the manufacture of a medicament identified for the treatment or prevention of diabetes.

According to another aspect of the present invention there is provided use of a cannabidiol for the manufacture of a medicament identified for the treatment or prevention of insulitis.

According to still further features in the described preferred embodiments the medicament is formulated for parenteral administration.

According to still further features in the described preferred embodiments the medicament is formulated for oral administration.

According to still further features in the described preferred embodiments the medicament is formulated for transdermal administration.

According to yet another aspect of the present invention there is provided use of a cannabidiol for the manufacture of a medicament for prolonging survival of transplanted pancreatic cells.

According to further features in preferred embodiments of the invention described below, the cannabidiol comprises a compound having the general formula:

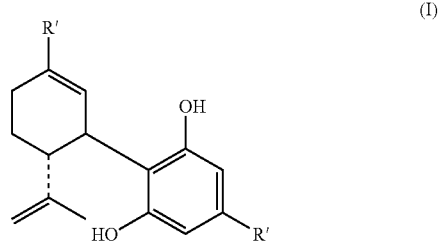

(I)

wherein R' is alkyl, COOH or CH2OH; and

R" is selected from the group consisting of a straight or branched alkyl having 5 to 12 carbon atoms; an —OR'", where R'" is straight or branched alkyl having 5 to 9 carbon atoms, or a straight or branched alkyl substituted at the terminal carbon atom by a phenyl group; and a —(CH$_2$)$_n$—O- alkyl group, where n is an integer from 1 to 7 and the alkyl group has 1 to 5 carbon atoms.

According to still further features in the described preferred embodiments R' is $CH_3$ and R" is a straight alkyl having 5 carbon atoms ($C_5H_{11}$).

According to still further features in the described preferred embodiments the cannabidiol comprises a natural cannabidiol.

According to still further features in the described preferred embodiments the natural cannabidiol is extracted from Cannabis.

The present invention successfully addresses the shortcomings of the presently known configurations by providing methods, uses and articles-of-manufacturing for treating or preventing diabetes and insulitis.

DESCRIPTION OF THE PREFERRED EMBODIMENTS

The present invention is of a method of treating or preventing diabetes and via administration of a cannabidiol. The present invention is further of an article-of-manufacturing which includes a cannabidiol and is identified for use in treatment or prevention of diabetes and related disorders.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Cannabidiol (CBD) is present in most Cannabis preparations (hashish, marijuana, ganja). It was first isolated by Adams [J. Amer. Chem. Soc., 6: 2194 (1940)] and its structure was elucidated by Mechoulam and Shvo in 1963 (Tetrahedron 19: 2073). The synthesis of cannabidiol in its racemic form and its natural form were reported in J. Amer. Chem. Soc. 87:3273-3275 (1965), and in Helv. Chim. Acta. 50:719-723 (1967).

It has been observed that CBD displays anticonvulsant activity [Pharmacol, 124: 141-146 (1982)], and antipsychotic activity in the case of schizophrenia [Psychopharmacol. 104: 260-264 (1991); J. Clin. Psychiatry 56: 485-486 (1995)].

Preliminary studies by Formukong et al. [Inflammation 12: 361-371 (1988)] showed that CBD inhibited PBQ-induced writhing in mice when administered orally at doses of up to 10 mg/kg. Topical administration of CBD to mice was also shown to reduce TPA-induced erythema, which is dependent upon prostaglandin release.

In an in vitro study, Coffey et al [Biochem. Pharmacol, 52: 743-751 (1996)] demonstrated that cannabidiol inhibited nitric oxide (NO) produced by mouse peritoneal macrophages activated by LPS and IFNγ. Watzl et al [Drugs of Abuse, Immunity and Immunodeficiency, Plenum Press, New York, pp. 63-70 (1991)] studied in vitro the effects of CBD on secretions of IL-1, IL-2, IL-6, TNFα and IFNγ by human leukocytes. They found that CBD in low concentrations increased IFNγ production, whereas in high concentrations (5-24 pg/ml) it completely blocked IFNγ synthesis, decreased IL-1 and TNFα, production and did not affect IL-2 secretion.

U.S. Pat. No. 6,410,588 describes the use of cannabidiol for treating inflammatory diseases such as rheumatoid arthritis, multiple sclerosis and Crohn's Disease, and medicinal preparations containing CBD for use in treating such diseases.

PCT/IL01/00537 describes pharmaceutical compositions comprising cannabidiol derivatives which have analgesic, antianxiety, anticonvulsive, neuroprotective, antipsychotic and anticancer activity.

Although the prior art teaches several potential therapeutic effects and uses of CBD it does not describe or suggest use of CBD or derivatives thereof in treating diabetes.

While reducing the present invention to practice the inventors of the present invention surprisingly uncovered that CBD effectively prevented and ameliorated diabetes in model animals. As is illustrated in the Examples section which follows, administration of CBD to NOD mice, which are commonly used as a model of human insulin-dependant diabetes mellitus, substantially reduced diabetes incidence and plasma INFγ levels, and prevented the onset of insulitis in the model animals, as compared with untreated or vehicle treated controls.

Thus, according to one aspect of the present invention, there is provided a method of treating or preventing diabetes.

The method of treatment according to the present invention is effected by administering to a subject, such as human subject, a pharmaceutically effective amount of a cannabidiol.

As used herein, the phrases "treating or preventing" and "treatment or prevention" encompass the complete range of therapeutically positive effects of administrating a cannabidiol to a subject including reduction of, alleviation of, and relief from, diabetes and illness, diabetes symptoms or diabetes related disorders. Treatment or prevention includes the prevention or postponement of development of the disease, prevention or postponement of development of symptoms such as, for example, hyperglycemia or glucosuria and/or a reduction in the severity of such symptoms that will or are expected to develop. These further include ameliorating existing symptoms, preventing additional symptoms and ameliorating or preventing the underlying metabolic causes of symptoms.

According to one preferred embodiment of the present invention, cannabidiol is administered to a human subject having diabetes or having at least one risk factor for developing diabetes.

Risk factors for developing type I diabetes include, but not limited to (i) having a blood relative with Type I diabetes; (ii) being diagnosed positive for autoantibody without overt Type 1 diabetes (e.g., cytoplasmic islet cell autoantibodies, insulin antibodies and glutamic acid decarboxylase autoantibodies; (iii) presence of histocompatibility (HLA) type DR3 or DR4DQW8; (iv) glucose abnormalities such as a loss of first phase insulin secretion on glucose tolerance tests. Risk factors for developing Type II diabetes include, but not limited to (i) obesity; (ii) hypertension; (iii) dyslipidemia (low HDL cholesterol level and/or high triglyceride level; (iv) cigarette smoking; (v) gestational diabetes; (vi) age; and (vii) low birth weight. Additional risk factors recognized by the American Diabetes Association are described hereinunder.

A subject having type I diabetes may be treated by transplantation of insulin producing pancreatic cells, either a solid-organ pancreas transplantation or a pancreatic islet transplantation (Stock and Bluestone, Ann. Rev. Med. 55:133-156, 2004). As a result of improved immunosuppression treatments, advances in surgical techniques, and enhanced availability of donors, the number of pancreas or Langerhans islet transplantations has been steadily growing (Robertson R. P, New Engl. J. Med. 327: 1861, 1992). However, the survival of transplanted islets remained poor due to immunogenic destruction (Kendall et al., The Endocrinologist 5:28-35, 1995; and Diabetes, American Diabetes Association, pp. 46-47, 1993). Recently, Jeffrey et al. (JAMA 290:2817-2823, 2003) reported that from 1995-2000, the survival of patients with diabetes and preserved kidney function receiving a solitary pancreas transplantation was significantly worse as compared with the survival of waiting-list patients receiving conventional therapy. Overall, the widespread application of pancreas transplantation depends on effectively protecting of the transplanted pancreatic cells from immunogenic destruction.

As illustrated in Examples 1-2 below, administration of a cannabidiol to NOD mice effectively suppressed diabetes and protected their Langerhans islets from immunogenic destruction (insulitis). Accordingly, 87% of the islets observed in samples obtained from cannabidiol-treated mice were protected during a 20 week period, as compared with 85% and 96% of totally infiltrated or fully destroyed islets observed in the untreated control and the vehicle-treated mice, respectively.

Thus, according to another aspect of the present invention, cannabidiol is administered to a subject having transplanted pancreatic cells, to thereby prolong survival of the pancreatic cells transplanted in the subject.

The phrase "prolong survival" refers to prolonging viability and biological function (e.g., insulin secretion) of the transplanted pancreatic cells.

The phrase "pancreatic cells" used herein refers to a whole or partially intact pancreas, pancreatic Langerhans islets, or isolated pancreatic cells. The cells may be autograft cells, allograft cells, xenograft cells, differentiated stem cells, or residual cells.

It will be appreciated that the cannabidiol utilized by the present invention is distinct and different from naturally occurring or synthetic cannabinoids in both chemical and biological properties.

The term "cannabinoid" refers to any natural or synthetic agonist of a cannabinoid receptor (e.g., CB1 and CB2). Naturally occurring cannabinoids may be divided into two categories, plant-derived and endogenous. Plant-derived cannabinoids are exemplified by the well-known $\Delta^9$-tetrahydrocannabinol (THC), the psychotropic principle in marijuana. Endogenous cannabinoids (endocannabinoids) are a class of lipid-like molecules that share receptor binding sites with plant-derived cannabinoids and mimic many of their neurobehavioral effects [Mechoulam et al., Adv. Exp. Bio. Med. 402:95-101 (1996)]. Two endocannabinoids have been characterized in some detail: arachidonyl ethanolamide (anandamide) [Devane et al., Science 258:1946-1949 (1992); Felder et al., Proc. Natl. Acad. Sci. USA. 90:7656-7660 (1993)] and 2-arachidonoyl glycerol (2-AG) [Mechoulam et al., Biochem. Pharmacol 50:83-90 (1995)].

In addition to the above, presently known cannabinoids include, for example, $\Delta^8$-THC, $\Delta^9$-THC-dimethylheptyl, 11-hydroxy-$\Delta^8$-THC-dimethylheptyl (HU-210), 5'-F-$\Delta^8$-THC, 11-OH-cannabinol, $\Delta^8$-THC-11-oic-dimethylheptyl acid, 1-deoxy-11-OH-$\Delta^8$-THC-dimethylheptyl (JWH-051), 11-Hydroxy THCs, desacetyl-L-nantradol, 11-OH-cannabinol-dimethylheptyl, cannabinol-dimethylheptyl-11-oic acid, HU-308, HU 243, L-759633, L-759656, L-768242, JWH-133, JWH-139, JWH-051, JWH-015, CP55940, CP47497, CP55244, R-(+)-WIN55212, ACEA, ACPA, 0-1812, 2-arachidonoylglyceryl ether, and methanandamide, and analogs or derivatives thereof. Additional cannabinoids are described in the references cited in the background section above.

Further additional natural or synthetic cannabinoids are described in U.S. Pat. Nos. 4,371,720, 5,013,387, 5,081,122, 5,292,736, 5,461,034, 5,618,955, 6,166,066 and 6,531,636; International Patent applications WO 01/9773, WO 97/29079, WO 99/02499, WO 98/41519, and WO 94/12466; European Patent Nos. EP 0570920 and EP 0444451; French Patent No. FR 2735774; and Israeli Pat. Nos. IL 01/00551 and IL 99/00187; Gaoni and Mechoulam, J. Amer. Chem. Soc. 93, 217 (1971); Mechoulam et al., Science 169, 611 (1970); Edery et al., Ann. N.Y. Acad. Sci., 191,40 (1971); Mechoulam et al., J. Amer. Chem. Soc., 94,7930 (1972); R. Mechoulam (ed.), "Marijuana: Chemistry, Metabolism, Pharmacology, and Clinical Effects" Academic Press, 1973, New-York; Houry et al., J. Med. Chem., 17, 287 (1974); Houry et al., J. Med. Chem., 18, 951 (1975); Mechoulam et al., Chem. Reviews, 76,75 (1976); Mechoulam et al., J. Med. Chem., 23, 1068 (1980); Srebnik et al., J. Chem. Soc., Perkin Trans. I, 2881 (1984); Mechoulam et al., Tetrahedron: Asymmetry, 1, 315 (1990); Devane et al., Science, 258,1946 (1992); Burstein et al., J. Med. Chem., 35, 3135 (1992); Hanus et al., J. Med. Chem., 36, 3032 (1993); Mechoulam et al., Biochem. Pharmacol., 50, 83 (1995); Sheskin et al., J. Med. Chem., 40, 659 (1997); Rhee et al., J. Med. Chem. 40, 3228 (1997); and Hanus et al., PNAS, 98, 3662 (2001).

Unlike cannabinoids such as described hereinabove, cannabidiol does not bind either the brain receptor CB1 or the peripheral receptors CB2 and therefore does not cause the central or peripheral effects mediated by these receptors. Furthermore, CBD has no psychotropic (cannabimimetic) activity and its molecular structure and properties are substantially different from those of cannabinoids [Science 169: 611-612 (1970); "Marijuana/cannabinoids: neurobiology and neurophysiology", ed. L. Murphy and A. Bartke, CRC Press, Boca Raton, 1-33 (1992)].

The cannabidiol of the present invention includes a natural cannabidiol and enantiomers and derivatives thereof having the general formula I described below:

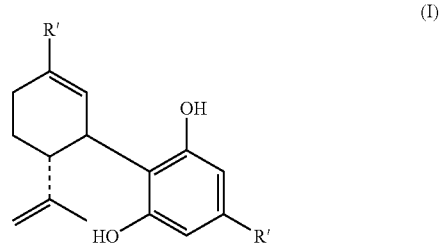

(I)

in which R' stands for alkyl, COOH or CH$_2$OH; and
R" stands for:
a. straight or branched alkyl of 5 to 12 carbon atoms;
b. a group —O—R''', where R''' is straight or branched alkyl of 5 to 9 carbon atoms, or a straight or branched alkyl substituted at the terminal carbon atom by a phenyl group; or
c. a group —(CH$_2$)$_n$—O-alkyl, where n is an integer from 1 to 7 and the alkyl group contains 1 to 5 carbon atoms.

According to one preferred embodiment of the present invention, the cannabidiol is a natural cannabidiol having formula I described above, wherein R'=CH$_3$ and R"=C$_5$H$_{11}$ A natural cannabidiol can be extracted from Cannabis using methods such as described, for example, in U.S. Pat. No. 6,403,123 and Gaoni and Mechoulam [J. Am. Chem. Soc. 93: 217-224 (1971)].

According to another preferred embodiment of the present invention, the cannabidiol is a synthetic cannabidiol or a derivative thereof having the general formula I described above, wherein R'=COOF and R"=1,1-dimethylheptyl.

A synthetic cannabidiol or a derivative thereof can be generated using methods such as described, for example, in PCT/IL01/00537.

Briefly, the process for the preparation of compounds of general formula I in which R'=CH$_2$OH and R"= a. straight or branched alkyl of 5 to 12 carbon atoms;

b. a group —O—R''', where R''' is straight or branched alkyl of 5 to 9 carbon atoms, or a straight or branched alkyl substituted at the terminal carbon atom by a phenyl group; or c. a group —(CH$_2$)$_n$—O-alkyl, where n is an integer from 1 to 7 and the alkyl group contains 1 to 5 carbon atoms.

starting from a compound of general formula I, in which R'=CH$_3$ and R" is one of the substituents indicated above, includes (i) blocking of the phenolic groups in order to allow further chemical transformations; followed by (ii) selective epoxidation of the ring double bond; (iii) selective opening of the epoxide ring to form an allylic alcohol; then several steps (iv, v, Vi, Vii) which by allylic rearrangement lead to the dimethoxy derivative of the desired compound. The final step (viii) involves demethoxylation under harsh conditions to form the desired allylic alcohol.

The cannabidiol described above can be used in therapy per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transdermal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in organic solutions, preferably in oily carriers, such as arachis oil, sesame oil, olive oil and similar carriers, or liposome carriers, to which yet other excipients may, if desired, be added, such as benzyl alcohol and benzyl benzoate One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

The pharmaceutical composition may be in the form of a suppository adapted for introduction into the rectal, vaginal or urethral orifice of the body. Preferably, the suppository formulation is solid at room temperature but melts or dissolves at body temperature. A suitable suppository carrier may include, for example, cocoa butter, glycerinated gelatin, a hydrogenated vegetable oils, a polyethylene glycols and a fatty acid ester of polyethylene glycol.

For transdermal administration, the composition may take the form of a patche, such as a multilaminate patch, containing the active principle and an appropriate solvent such as, for example, glycerin, propylene carbonate, and propylene glycol. Preferably, the transdermal delivery of cannabidiol is effected by using ethosomal carriers such as described, for example, by Lodzki et al. (J. Conttrol Release 93: 377-387, 2003.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include suspensions of the active ingredients which may be prepared as appropriate oily or water based injection suspensions. Suitable lipophilic solvents or vehicles include fatty oils such as sesame oil, arachis oil, sesame oil, olive oil or synthetic fatty acids esters such as ethyl oleate or triglycerides.

Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

A pharmaceutical composition for parenteral administration may include a liposome carrier. A liposome contains one or more concentric lipid bilayers separated by aqueous compartments, and having and aqueous core compartments. A liposome can be used to deliver hydrophobic compounds, such as cannabidiol, by incorporation of the compound into the lipid bilayer, or may be used to deliver cannabidiol by encapsulation of the compound in the aqueous compartments or core space. Suitable liposomes are described, for example, in U.S. Pat. Nos. 4,427,649 and 5,795,587.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., mammary tumor progression) or prolong the survival of the subject being treated.

Determination of a therapeutically effective amount is well within the capability of those skilled in the art. For any preparation used in the methods of the invention, the therapeutically effective amount or dose can be estimated initially in an animal model, such as the NOD mice described in the Examples section which follows, to achieve a desired concentration. Preferably, the effective amount of a cannabidiol being administered to a human subject ranges between 0.1 to 100 mg cannabidiol per day.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to, for example, reduce glucosuria or hyperglycemia in diabetic subjects. Methods of monitoring glucosuria are routine and well known in the art such as, for example, Combi Teststrips (Medi-Test, Macherey-Nagel, Duren, Germany). Similarly, methods of monitoring plasma glucose levels are routine and well known in the art such as, for example, using Glucose Analyzer 2 (Beckman Instruments).

The minimal effective concentration of cannabidiol will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment or prevention of an indicated condition, as if further detailed above.

Thus, the present invention provides novel methods and articles of manufacture for use in treatment or prevention of diabetes, insulitis and related disorders.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Preventing Diabetes in NOD Mice by Administering Cannabidiol

Materials and Methods:

Animals: Non-obese diabetic (NOD) mice develop spontaneous autoimmune diabetes and are commonly used as an experimental model for human insulin-dependent diabetes mellitus [Miazaki A., Clin. Exp. Immunol. 60:622 (1998); Harada, M., Exp. Clin. Endocrinol. 89: 251 (1987)].

Six to twelve week old NOD/Ltj female mice were fed standard laboratory animal chow ad libitum and were kept in Specific Pathogen Free (SPF) animal house facility.

Experimental design: Cannabidiol (CBD) was extracted and purified from Cannabis plant as described by Gaoni and Mechoulam (J. Am. Chem. Soc. 93: 217-224, 1971). The purified CBD was dissolved in a solution of alchohol:chremophor-el:saline at a ratio of 1:1:18 and was administered to mice intraperitoneally at a dose of 5 mg a.i/kg (100 µg per mouse), five i.p. injections per week for a total of 10-23 injections. Mice injected with vehicle alone as well as untreated mice served as controls.

Glucosuria analysis: The severity of diabetes was determined according to glucosuria, which was measured using Combi 9 Teststrips (Medi-Test, Macherey-Nagel, Duren, Germany).

Intraperitoneal glucose tolerance tests (IPGTT): Blood samples were obtained from the paraorbital plexus at 0 and 60 minutes after administration of an i.p. glucose injection at a dose of 1 g/kg body weight. Plasma glucose levels were determined using Glucose Analyzer 2 (Beckman Instruments). A glucose level above 15 mmol/liter at the 60 min time point was considered as a positive IPGTT.

Plasma INFγ: INFγ is associated with the progression of diabetes in NOD mice (Schloot, N. C., Diabetes Metab. Res. Rev. 18:64, 2002; Weiss et al., Cytokine 19:85, 2002; Braz, J., Med. Biol. Res. 35: 1347, 2000).

Plasma INFγ levels in mice were determined by ELISA kit (B.D Bioscience San Diego U.S.A).

Histopathology: Twenty weeks after onset of treatment mice were sacrificed. Pancreatic tissue samples were fixed in 4% buffered formation, embedded in paraffin, sectioned (5 µm thickness) and stained with hematoxylin and eosin. The stained pancreatic sections were observed under a microscope for infiltration of mononuclear lymphocytes into the islets of Langerhans (insulitis). The sections were scored by two uninformed observers as follows: 0, no cell infiltration; 1, cell infiltration in <20% of islet area; 2, cell infiltration in <50% of islet area; cell infiltration in <75% of islet area; and 4, cell infiltration in 90-100% of islet area.

Results:

As can be seen in Table 1 below, 86.4 (19/22) and 69.2% (9/13) of untreated and vehicle treated mice, respectively, developed diabetes. On the other hand, only 21.7% (5/23) of the CBD-treated mice developed diabetes under the experimental conditions, representing a greater than 65% rate of protection. It is important to note, however, that the onset of symptoms in the 5 CBD-treated diabetic mice was substantially delayed compared to untreated and vehicle-treated controls.

TABLE 1

The effect of CBD on the incidence of diabetes developed in NOD mice

| Treatment | Total No. of mice | No. of diabetic mice | Diabetes incidence (%) | Diabetes appearance[1] (weeks) |
|---|---|---|---|---|
| Untreated control | 22 | 19 | 86.4 | 14 (10-20) |
| Vehicle | 13 | 9 | 69.2 | 16.6 (14-26) |
| CBD | 23 | 5 | 21.7 | 18.4 (15-22) |

[1]The mean and range of weeks of first positive diagnosis.

As can be seen in Table 2 below, the plasma INFγ level in CBD-treated mice (43 pg/ml) was significantly lower (p<0.05) than in untreated and vehicle control mice (107 and 94 pg/ml, respectively).

TABLE 2

The effect of CBD on plasma INFγ level in NOD mice

| Treatment | INFγ (pg/ml)[1] ± SD |
|---|---|
| Untreated control | 107 ± 41 |
| Vehicle | 94 ± 41 |
| CBD | 43 ± 21*[2] |

[1]Each value represents a mean of 5 mice (replications).
[2]Value was significantly different from untreated and vehicle controls at p < 0.05.

As can be seen in Table 3 below, administration of CBD significantly prevented or inhibited the insulitis characteristic of autoimmune diabetes. Analysis of sections of pancreatic tissue from untreated control and vehicle treated mice revealed 85% (62/73) and 96% (50/52), respectively, of totally infiltrated or fully destroyed islets, indicating widespread insulitis. Intact and partially infiltrated islets in the untreated controls and vehicle-treated mice were observed in only 3.8% and 15.1% of the pancreas samples obtained from vehicle treated and untreated mice, respectively. In samples from the CBD-treated mice, on the other hand, 87% (47/54) of the CBD-treated mice were protected, demonstrating intact (48%, 26/54) or only partially infiltrated pancreatic islets (39%, 21/54), while only 11% (6/54) and 1.9% (1/54) of the islets showed total infiltration or destruction, respectively.

TABLE 3

The effect of CBD on the appearance of insulitis in NOD mice

| Treatment | No. of scored fields | No. of intact islets | No. of partially infiltrated islets | No. of totally infiltrated islets | No. of fully destroyed islets |
|---|---|---|---|---|---|
| Untreated control | 73 | 4 | 7 | 11 | 51 |
| Vehicle | 52 | 0 | 2 | 29 | 21 |
| CBD | 54 | 26 | 21 | 6 | 1 |

The results presented hereinabove clearly show that administration of cannabidiol substantially delays onset and ameliorates diabetes and insulitis in model animals.

Example 2

Cannabidiol Suppressing diabetes in male NOD mice induced with the disease

Animals—See Example 1, Above.

Experimental design—Male NOD mice were irradiated (650 cGy), 24 hrs prior to intravenous injection of spleen cells ($25\text{-}28\times10^6$) derived from female diabetic mice. The injected mice were divided into three groups including untreated control; vehicle treated mice (20 IP injections, 5 times/week); and CBD treated mice (5 mg/kg CBD, 20 IP injections, 5 times/week).

Intraperitoneal glucose tolerance tests (IPGTT)—see Example 1 above. Blood glucose levels above 140 mg/dl were considered diabetic by testing blood glucose at t-0, 60 min following IP injection of 1 gr/Kg body weight of glucose [Glucometer Elite apparatus (Bayer Diagnostics, ELKART, IN)]. Alternatively, urine samples were taken twice a week from diabetic mice for testing glucose levels. Urine glucose levels above 1000 mg/dl as determined by combi 9 Teststrips (Medi-Test, Macherey-Nagel, Duren, Germany) were considered diabetic;

Results

The effect of CBD was tested on a more progressive stage of diabetes. To this end a large number of diabetic cells were transferred to male NOD mice.

Diabetic developed in all the animals thus injected. As can be seen in Table 4 below, CBD suppressed the appearance of diabetes by about half in male NOD mice which were initially injected with splenocytes from diabetic female NOD mice.

TABLE 4

CBD protects male NOD mice from induced diabetes

| Treatment | Total No. of Mice | No. of mice w/ latent diabetes* | No. of diabetic mice** | Total % of diabetic mice |
|---|---|---|---|---|
| Untreated Control | 6 | 2 | 4 | 100% |
| Vehicle | 13 | 3 | 8 | 85% |
| CBD | 15 | 2 | 6 | 53% |

*mice with blood glucose levels above 140 mg/dl 60 minutes following IP glucose injection.
**mice with urine glucose levels above 1000 mg/dl.

These results clearly demonstrate that CBD can suppress a progressive state of diabetes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

What is claimed is:

1. A method of treating Type II diabetes in a subject, the method comprising administering to the subject a therapeutically effective amount of cannabidiol (CBD), wherein said cannabidiol is comprised in a composition having no psychotropic activity, thereby treating type II diabetes in the subject.

2. The method of claim 1, wherein said administering is via parenteral administration.

3. The method of claim 1, wherein said administering is via oral administration.

4. The method of claim 1, wherein said administering is via transdermal administration.

5. The method of claim 1, wherein said subject has transplanted pancreatic cells.

* * * * *

UNITED STATES PATENT AND TRADEMARK OFFICE
CERTIFICATE OF CORRECTION

PATENT NO.        : 8,071,641 B2                                         Page 1 of 1
APPLICATION NO.   : 10/589623
DATED             : December 6, 2011
INVENTOR(S)       : Lola Weiss et al.

It is certified that error appears in the above-identified patent and that said Letters Patent is hereby corrected as shown below:

On the title page after:

"Yissum Research Development Company of the Hebrew University of Jerusalem, Jerusalem (IL)"

delete the following word:

"Hadasit"

Signed and Sealed this

Thirteenth Day of October, 2015

Michelle K. Lee
*Director of the United States Patent and Trademark Office*